United States Patent
Umino et al.

[11] Patent Number: 5,935,534
[45] Date of Patent: Aug. 10, 1999

[54] CRYSTALLIZATION METHOD

[75] Inventors: Hiroshi Umino; Hiromitsu Shibuya; Nobuyasu Chikamatsu; Kazuo Kikuchi, all of Yokohama; Masahiko Yamagishi; Kiyoshi Takahashi, both of Yokkaichi, all of Japan

[73] Assignees: JGC Corporation; Mitsubishi Chemical Corporation, both of Tokyo, Japan

[21] Appl. No.: 08/758,502

[22] Filed: Dec. 2, 1996

[30] Foreign Application Priority Data

Dec. 1, 1995 [JP] Japan .................................. 7-338139

[51] Int. Cl.⁶ ........................................ B01D 9/00
[52] U.S. Cl. .......................... 422/245.1; 117/11
[58] Field of Search .................... 117/1, 2, 3, 4, 117/5, 11; 422/245.1

[56] References Cited

U.S. PATENT DOCUMENTS

| 3,282,968 | 11/1966 | Scribner et al. | 552/305 |
| 4,081,485 | 3/1978 | Eguchi | 568/312 |
| 4,780,568 | 10/1988 | Pascoe | 562/599 |

FOREIGN PATENT DOCUMENTS

| 0 648 520 A1 | of 1994 | European Pat. Off. . |
| 0 616 998 A1 | 4/1995 | European Pat. Off. . |
| 2 341 343 | 9/1977 | France . |
| 7-48311 | 2/1995 | Japan . |
| 7-163802 | 6/1995 | Japan . |

OTHER PUBLICATIONS

Handbook of Industrial Crystallization, Allan S. Myerson, Butterworth–Heinemann, 1993 Japanese Literature Article entitled, Introduction to Easy Practical Crystallization Process (pp. 76–83) (English summary attached).

*Primary Examiner*—Felisa Hiteshew
*Attorney, Agent, or Firm*—McDermott, Will & Emery

[57] ABSTRACT

In a crystallization method, a liquid mixture containing a crystallizable component is cooled so as to form and separate crystals of the crystallizable component. Then, a purified melt having purity substantially equal to that of the separated crystals, to which a polymerization inhibitor is added and which is heated to a temperature higher than a freezing point of the separated crystals, is circulated to flow contacting the crystals so as to accelerate melting. Then, the melted crystals are recovered along with the purified melt containing the polymerization inhibitor.

6 Claims, 6 Drawing Sheets

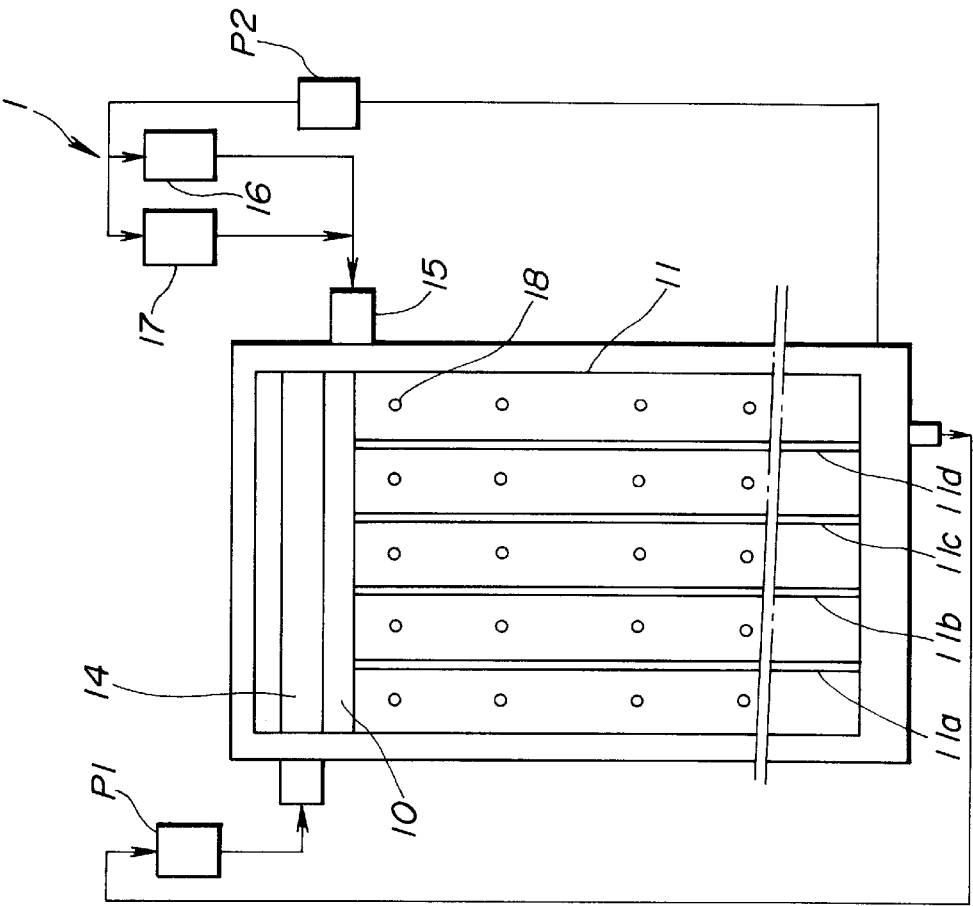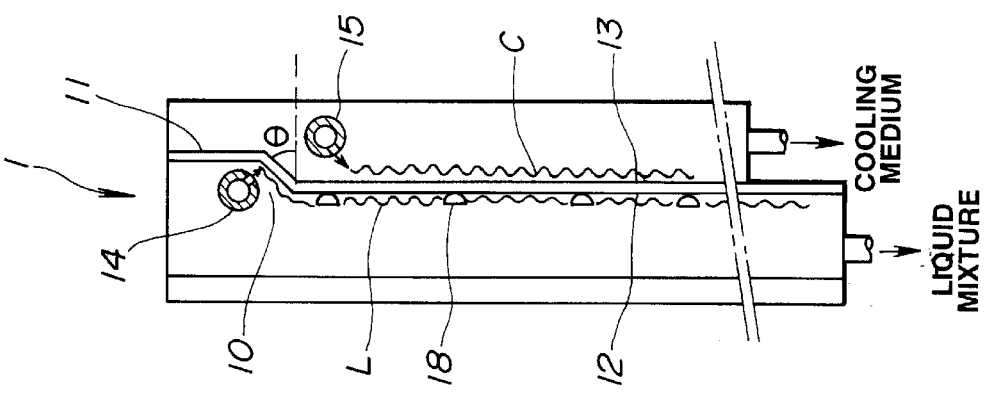

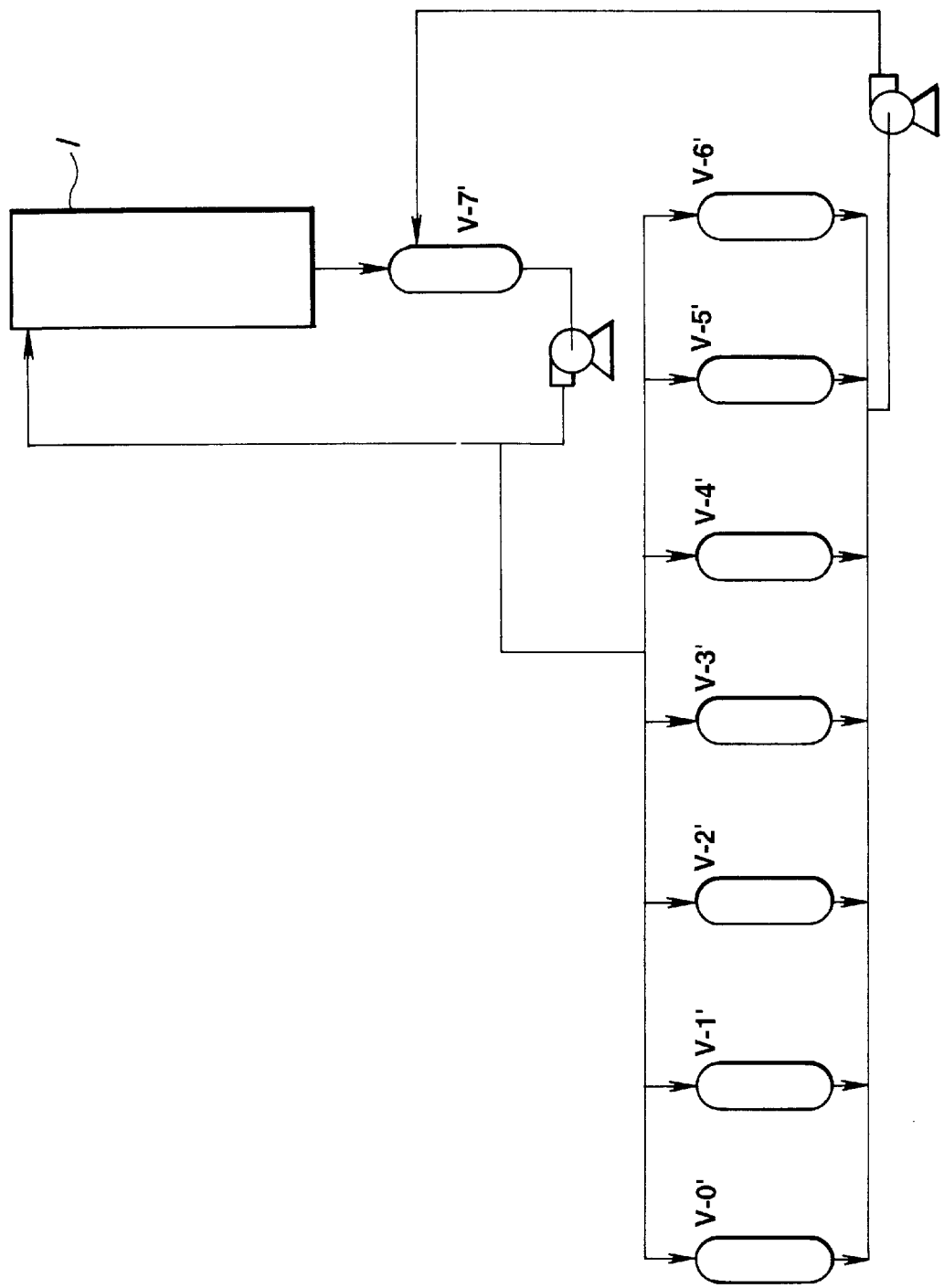

5,935,534

CRYSTALLIZATION METHOD

BACKGROUND OF THE INVENTION

1. Field of the Invention

The present invention relates to a crystallization method for obtaining high-purity products by crystallization from liquid mixtures containing crystallizable components and, in particular, to a crystallization method suitable for large-scale and multi-stage purification of acrylic acid and methacrylic acid.

2. Description of the Prior Art

For example, commercially produced acrylic acid usually contains such impurity components as acetic acid and propionic acid. The concentrations of these impurities are about 0.1% in total. However, due to recent expansion of usage, very high-purity acrylic acids with impurity concentrations in the order of some tens to hundreds of ppm are required, for example, for paper diapers.

In general, impurities are removed by distillation. However, it is very difficult to remove such impurities as acetic acid and propionic acid by distillation since these impurity components have boiling points close to that of acrylic acid. Under such circumstances, it has been proposed to remove these impurities by crystallization.

Two typical crystallization methods are available; one being that seed crystals are put into a liquid mixture containing a crystallizable component so as to nucleate and grow crystals in a suspended state in the liquid, and the other being that crystals are grown on cooled surfaces. In case of large-scale processes, particularly when producing a large quantity of adhesive crystals, such as acrylic acid, the latter method is suitable for it, but the former method is not. The technique employing the latter method for purification of acrylic acid and methacrylic acid is disclosed in, for example, Japanese First (unexamined) Patent Publication No. 7-48311 and Japanese First (unexamined) Patent Publication No. 7-163802.

The former publication discloses a technique, wherein a dynamic crystallization apparatus and a static crystallization apparatus are combined so as to perform multi-stage crystallization. In the dynamic crystallization apparatus, acrylic acid containing impurities (feed liquid mixture) is introduced to flow down on an inner surface of a vertical tube and, by cooling the surface, the crystals grow on the inner surface. On the other hand, in the static crystallization apparatus, the mother liquor obtained through the dynamic crystallization apparatus is introduced into a tank equipped with cooling coils and crystals are formed on the surfaces of the cooling coils.

The latter publication discloses a technique, wherein multi-stage crystallization is performed using a crystallizer having vertical plates and tanks. Specifically, a liquid mixture is introduced to flow down on one surface of the plate and, by cooling the plate from an opposite side, crystals are formed on the one surface of the plate. Further, the mother liquor, the sweated liquid and the melt obtained through crystallization using the liquid mixture in one of the tanks as a feed are sent to different tanks, and obtained melt is further crystallized.

On the other hand, it is possible that polymerizable substances, such as acrylic acid or methacrylic acid, are subjected to polymerization due to, for example, temperature rise or contamination with substances such as iron rust which can initiate polymerization. Further, heat generated by polymerization possibly causes vigorous reaction or explosion. In view of this, a polymerization inhibitor is added in advance in a polymerizable feed liquid before crystallization. The polymerization inhibitor is also added in advance in a final purified liquid (product).

Experiments conducted by the present inventors have revealed that the polymerization inhibitor is not contained in the crystals in the course of crystallization, but concentrated into the mother liquor. Thus, if the crystals containing substantially no polymerization inhibitor are melted, polymerization possibly occurs upon melting crystals, upon transferring the melt or during storing the melt in a tank which constitutes the multi-stage crystallization system.

SUMMARY OF THE INVENTION

Therefore, it is an object of the present invention to provide an improved crystallization method.

According to one aspect of the present invention, a crystallization method, wherein, after cooling a liquid mixture containing a crystallizable component, forming crystals of the component and separating the crystals, the separated crystals are melted and recovered as a melt so as to purify the component, comprises the steps of adding a polymerization inhibitor to a purified melt whose purity is substantially equal to that of the separated crystals; heating the purified melt to a temperature higher than a freezing point of the crystals; sending the heated melt to the crystals so as to melt the crystals; and recovering the melted crystals along with the purified melt containing the polymerization inhibitor.

It may be arranged that the polymerization inhibitor is added to the purified melt so that a concentration of the polymerization inhibitor in a sum of the melted crystals and the purified melt becomes higher than 10 ppm by weight.

According to another aspect of the present invention, a crystallization method comprises a crystallization step of cooling a liquid mixture containing a crystallizable component, forming crystals of the component and separating the crystals; and a melting step of the separated crystals and recovering a melt of the crystals; the crystallization and melting steps performed in a multi-stage manner to achieve multi-stage crystallization so as to gradually increase purity of the crystallizable component, wherein, in the crystallization step at a final purification stage of the multi-stage crystallization, a liquid mixture containing a polymerization inhibitor is used, and wherein, in the melting step at the final purification stage of the multi-stage crystallization, a polymerization inhibitor is added to a purified melt obtained in advance through the melting step at the final purification stage, and the purified melt is heated and sent onto the separated crystals so as to melt all the separated crystals, and the melted crystals are recovered along with the purified melt containing the polymerization inhibitor.

It may be arranged that the polymerization inhibitor is added to the purified melt so that a concentration of the polymerization inhibitor in a sum of the melted crystals and the purified melt becomes higher than 10 ppm by weight.

According to another aspect of the present invention, a crystallization method, wherein, using a crystallization system having a crystallizer equipped with cooling means for cooling a liquid mixture containing a crystallizable component and separating crystals of the component and melting/recovering means for melting the separated crystals and recovering a melt of the crystals, and further having first to Nth ($3 \leq N$) storage tanks, the crystallization is applied, by the crystallization system, to the liquid mixture in the Kth ($K<N$) storage tank so as to store a residual liquid in the (K−1)th storage tank, and further to store the melt of the crystals in the (K+1)th storage tank, a purified melt in the (K+1)th storage tank is heated and sent onto the crystals during the step to melt the separated crystals of the liquid mixture in the Kth storage tank, and (N−1)-stage crystallization is performed to achieve the process steps to the liquid mixtures in the first to (N−1)th storage tanks, comprises the steps of supplying a polymerization inhibitor only to the (N−1)th storage and Nth storage tanks when the feed liquid mixture is supplied to one of the first to (N−2)th storage tanks from outside of the crystallization system, while supplying the polymerization inhibitor only to the Nth storage tank when the feed liquid mixture is supplied to the (N−1)th storage tank from outside of the crystallization system.

It may be arranged that, after the crystals of the liquid mixture in the Kth storage tank are separated, partial melting of the crystals is performed before melting all the separated crystals, and that the melt of the crystals obtained by the partial melting is stored in the Kth storage tank.

BRIEF DESCRIPTION OF THE DRAWINGS

The present invention will be understood more fully from the detailed description given hereinbelow, taken in conjunction with the accompanying drawings.

In the drawings:

FIGS. 1A and 1B are a side view and a front view, respectively, of a crystallizer to be used in first to third preferred embodiment of the present invention;

FIG. 6 is a diagram showing a crystallization system for carrying out a crystallization method according to the third preferred embodiment of the present invention.

DESCRIPTION OF THE PREFERRED EMBODIMENT

Figure 2:
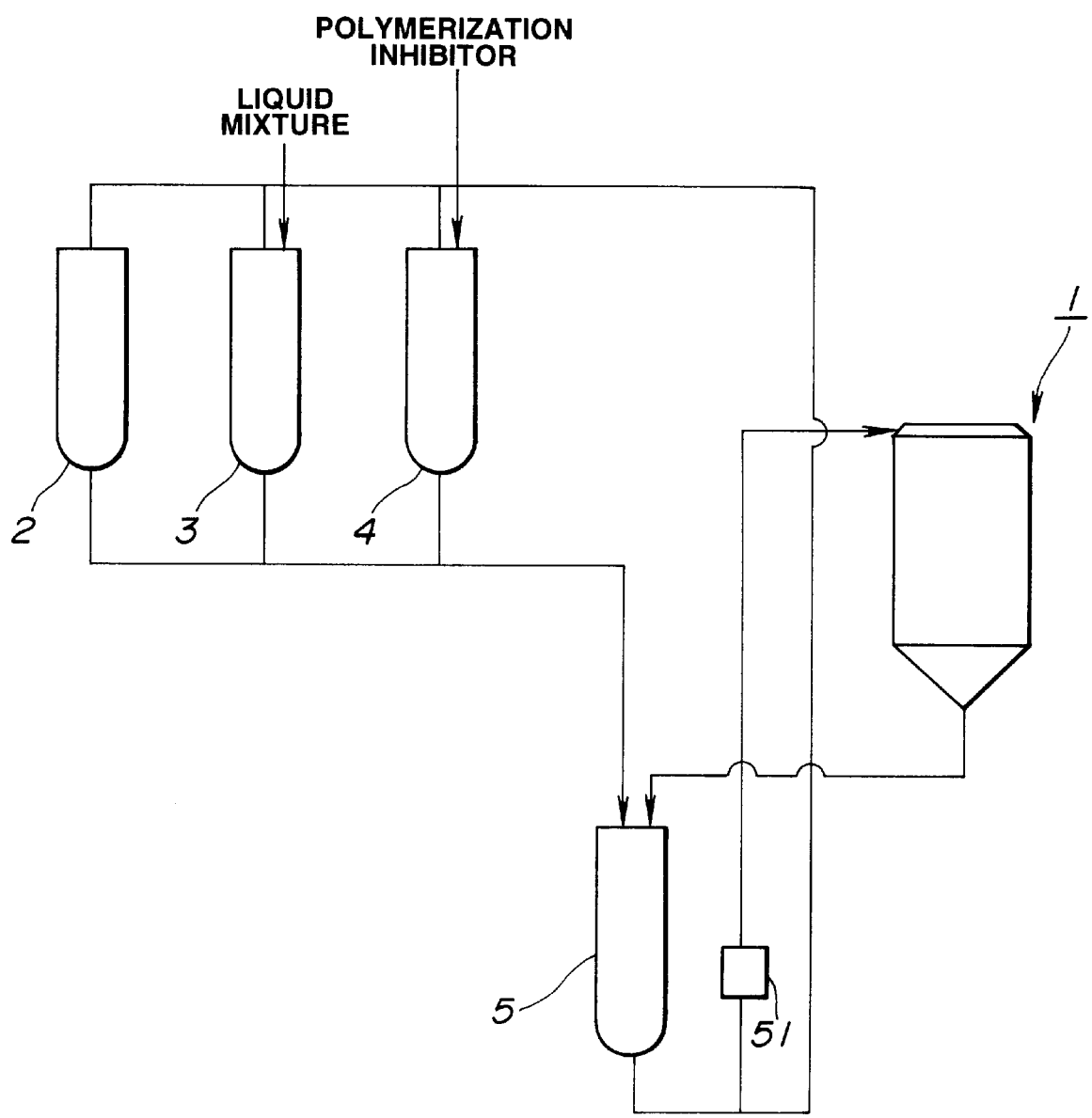
FIG. 2 is a diagram showing a crystallization system for carrying out a crystallization method according to the first preferred embodiments of the present invention.

The first preferred embodiment of the present invention will be described hereinbelow with reference to FIGS. 1A, 1B and 2.

FIGS. 1A and 1B show one example of a crystallizer 1 to be used in a crystallization system described later in this preferred embodiment. As appreciated from later description, the crystallizer 1 may be used in each of crystallization systems in all the preferred embodiments. In the figures, the crystallizer 1 includes a flat plate 11 on which crystals are formed. In this preferred embodiment, the plate 11 is made of stainless steel and has the size of 2 m (length)×1 m (width)×1 mm (thickness). The plate 11 is vertically arranged while being bent to provide an inclined surface 10 at its upper end portion. The crystallization region of the plate 11 is divided into, for example, five subregions in a lateral direction by partition plates 11a, 11b, 11c and 11d. At the upper side of the plate 11, a liquid distributor 14, working as liquid feeding means, is provided for feeding a liquid mixture L onto the inclined surface 10 directly or via a vertical surface continuous with the upper end of the inclined surface 10, so that the liquid mixture L flows down on one vertical surface 12 of the plate 11 as a film.

On the other hand, a cooling medium feed pipe 15, working as cooling medium feeding means, is provided at the opposite side of a vertical surface 13 of the plate 11 for feeding a cooling medium C of a temperature lower than a freezing point of the liquid mixture L so that the cooling medium C flows down on the opposite vertical surface 13 as a film. The cooling medium feed pipe 15 also works as a heating medium feed pipe, working as heating medium feeding means, for feeding a heating medium H of a temperature higher than the freezing point of the liquid mixture L onto the opposite vertical surface 13 of the plate 11. Symbols P1 and P2 represent pumps. The liquid mixture L which flows down on the one vertical surface 12 is circulated to the liquid distributor 14 via the pump P1, while the cooling medium C which flows down on the opposite surface 13 is circulated to the cooling medium feed pipe 15 via the pump P2 and a cooler 16. The cooling medium and the heating medium may be separately provided or the same medium may be used as the cooling or heating medium, that is, one heat transfer medium (HTM) may be used as the cooling medium when cooled and as the heating medium when heated. During a melting step, the heat transfer medium is heated to a predetermined temperature using a heater 17. On the one vertical surface 12 of the plate 11, a plurality of accessories 18 are attached vertically in a line at regular intervals to prevent crystals from peeling off the plate and falling down.

In the crystallizer 1 thus structured, the liquid mixture containing acrylic acid as a crystallizable component and impurities is circulated to flow down on the one vertical surface 12 as a film, while the cooling medium of a temperature lower than the freezing point of the liquid mixture is introduced and flows down on the opposite vertical surface 13 as a film. In order to produce uniform thicknesses of the films of the liquid mixture, supplying flow rates of the liquid mixture are, although it depends on the physical properties of the liquid mixture, particularly, surface tension thereof, preferably no smaller than 0.1 ton/h (0.1 tons per hour) per 1 meter width of the plate, and more preferably no smaller than 0.25 ton/h per 1 meter width of the plate. The upper limit of the supplying flow rates are not necessarily defined as long as the liquid mixture flows as a film. Since the heat transfer coefficient increases as the flow rate increases, the larger flow rate is desirable as is possible. The temperatures of the liquid mixture are preferably within +5° C., more preferably within +1° C. above the freezing point of the liquid mixture.

The cooling medium is obtained by cooling a heat transfer medium, such as an ethanol aqueous solution, via the cooler 16. The temperatures of the cooling medium are not particularly limited as long as they are lower than the freezing point of the liquid mixture. On the other hand, at the initial stage of the crystallization where crystallization begins, rapid crystallization lowers the purity of the crystals, therefore temperatures of the cooling medium are preferably in the range between the freezing point of the liquid mixture minus 20° C. and the freezing point of the liquid mixture. By cooling acrylic acid in this manner, the crystals of acrylic acid are formed on the one vertical surface 12 of the plate 11. After a thickness of the crystal layers reaches a predetermined value, the mother liquor, that is, the residual liquid mixture, is drained off. It is to be appreciated that, when the thickness of the crystal layer is too thin, the impurities tend to be trapped within the crystal layers lowering the purity thereof. On the other hand, when the thickness becomes too thick, the conductive heat flux through the crystal layer is reduced to prolong the time for crystallization. Accordingly, the thicknesses of the crystal layers are preferably 5 mm to 20 mm, and more preferably, 7 mm to 15 mm.

Thereafter, the heat transfer medium is heated via the heater 17 to a temperature higher than the freezing point of the crystals of acrylic acid to prepare the heating medium which is then introduced to flow down on the opposite vertical surface 13 of the plate 11. Simultaneously, the melt of the crystals of acrylic acid (purified melt) obtained in advance is heated and circulated to flow down on the one vertical surface 12 of the plate 11. As a result, the crystal layer of acrylic acid is heated from both sides and thus melted in a short time.

Although a polymerization inhibitor is added in advance into the feed liquid mixture supplied from outside of the later-described crystallization system, the polymerization inhibitor is hardly contained in the crystals of acrylic acid and, even if contained, the concentration is too low to inhibit polymerization.

In this preferred embodiment, after cooling the liquid mixture containing the crystallizable component, forming crystals of the component and separating crystals, the purified melt with purity substantially equal to that of separated crystals, provided with the polymerization inhibitor and heated to a predetermined temperature, is introduced to flow down on the one vertical surface 12 of the plate 11. Accordingly, the separated crystals adhered to the one vertical surface 12 is rapidly melted due to the heated purified melt, and further, since the separated crystals are melted in the presence of the inhibitor, polymerization can be prevented. Further, the polymerization inhibitor exists in the melt flowing down from the plate 11 (that is, the mixture of the heating purified melt and the melted crystals on the plate 11). Thus, polymerization never occurs upon melting of the crystals of acrylic acid, upon transferring the purified melt or while storing the purified melt in a storage tank.

As described above, the purified melt containing the polymerization inhibitor has the purity substantially equal to that of the crystals to be melted at that time. Specifically, it is preferable to use the purified melt in the same purification stage in the multi-stage crystallization process, but the melt obtained otherwise can also be used.

When performing the foregoing crystallization process, it is preferable to perform sweating process before all the crystals are melted. The sweating process is carried out by partially melting the crystal layers to remove high-concentration impurities trapped within the crystals or adhered to the crystal surfaces, so as to further decrease impurity concentration of the crystals. Specifically, before all the crystals are melted, the heating medium whose temperature is within ±5° C. of a melting point of the crystals, is introduced to the opposite vertical surface 13 as a film so as to partially melt the crystal layers. Accordingly, when performing the sweating process, the heat transfer medium is heated via the heater 17 to the temperature lower than that for the completely melting process.

FIG. 2 shows a single-stage crystallization system incorporating the foregoing crystallizer 1 for performing the single-stage crystallization process. In the figure, numerals 2 to 4 denote first to third storage tanks, respectively, and numeral 5 denotes a circulation tank. In this crystallization system, a liquid mixture of acrylic acid containing impurities, such as acetic acid or propionic acid, and a polymerization inhibitor is supplied into the second storage tank 3. The supplied liquid mixture is sent to the circulation tank 5, and then circulated to the crystallizer 1 where the crystals of acrylic acid are formed.

The residual liquid mixture (mother liquor) obtained through this process is then sent to the first storage tank 2 from the circulation tank 5. Subsequently, the sweating process (partial melting) is applied to the crystals of acrylic acid in the crystallizer 1 as described before, and a sweated liquid obtained through the sweating process is sent to the second storage tank 3. Thereafter, the purified melt in the third storage tank 4 is sent to the circulation tank 5, and then heated via heat exchanger 51 to the temperature higher than the freezing point of acrylic acid. The heated purified melt is then fed into the crystallizer 1 so as to melt the crystals of acrylic acid in cooperation with the simultaneous circulation of the heating medium as described before.

To the purified melt in the third storage tank 4, the polymerization inhibitor is added via an inhibitor feed pipe provided at the third storage tank 4. By providing an agitator in the third storage tank 4, the polymerization inhibitor concentration in the purified melt can be uniform.

The purified melt in the third storage tank 4 is obtained by purifying the liquid mixture in the second storage tank 3 in a process prior to the current crystallization process and thus has purity substantially equal to that of the crystals currently formed in the crystallizer 1.

With the foregoing arrangements, polymerization of acrylic acid never occurs not only during storage, transfer and heating of the purified melt, but also upon melting of the crystals which contain substantially no polymerization inhibitor. Instead of providing the inhibitor feed pipe to the third storage tank 4, an inhibitor feed pipe may be provided to the circulation tank 5 where the purified melt and the polymerization inhibitor are mixed. Alternatively, a mixing tank is separately provided where the polymerization inhibitor is added to the purified melt to prepare a polymerization inhibitor solution, which is then transferred to the third storage tank 4.

Figure 4:
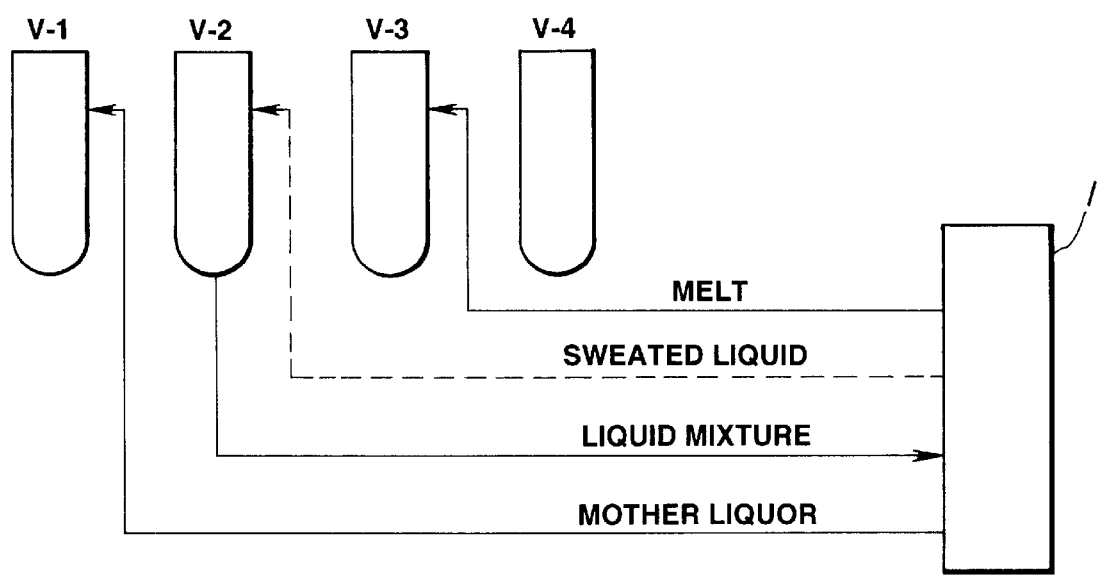
FIG. 4 is a diagram for explaining liquid flows in the crystallization system shown in FIG. 3.
Figure 5:
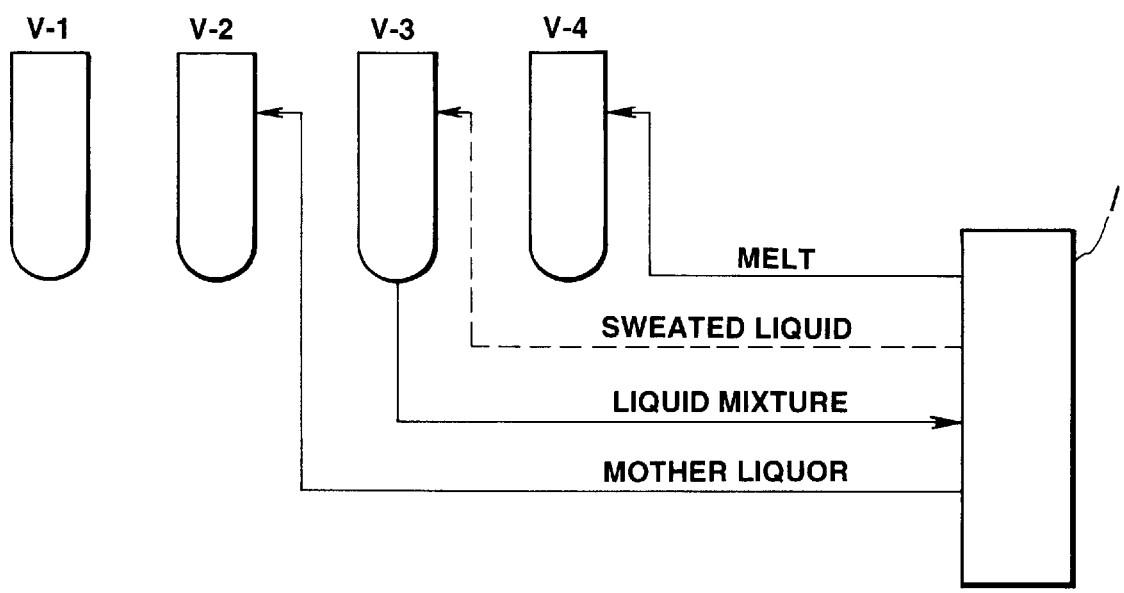
FIG. 5 is a diagram for explaining liquid flows in the crystallization system shown in FIG. 3.

Now, the second preferred embodiment of the present invention will be described hereinbelow with reference to FIGS. 3 to 5.

Figure 3:
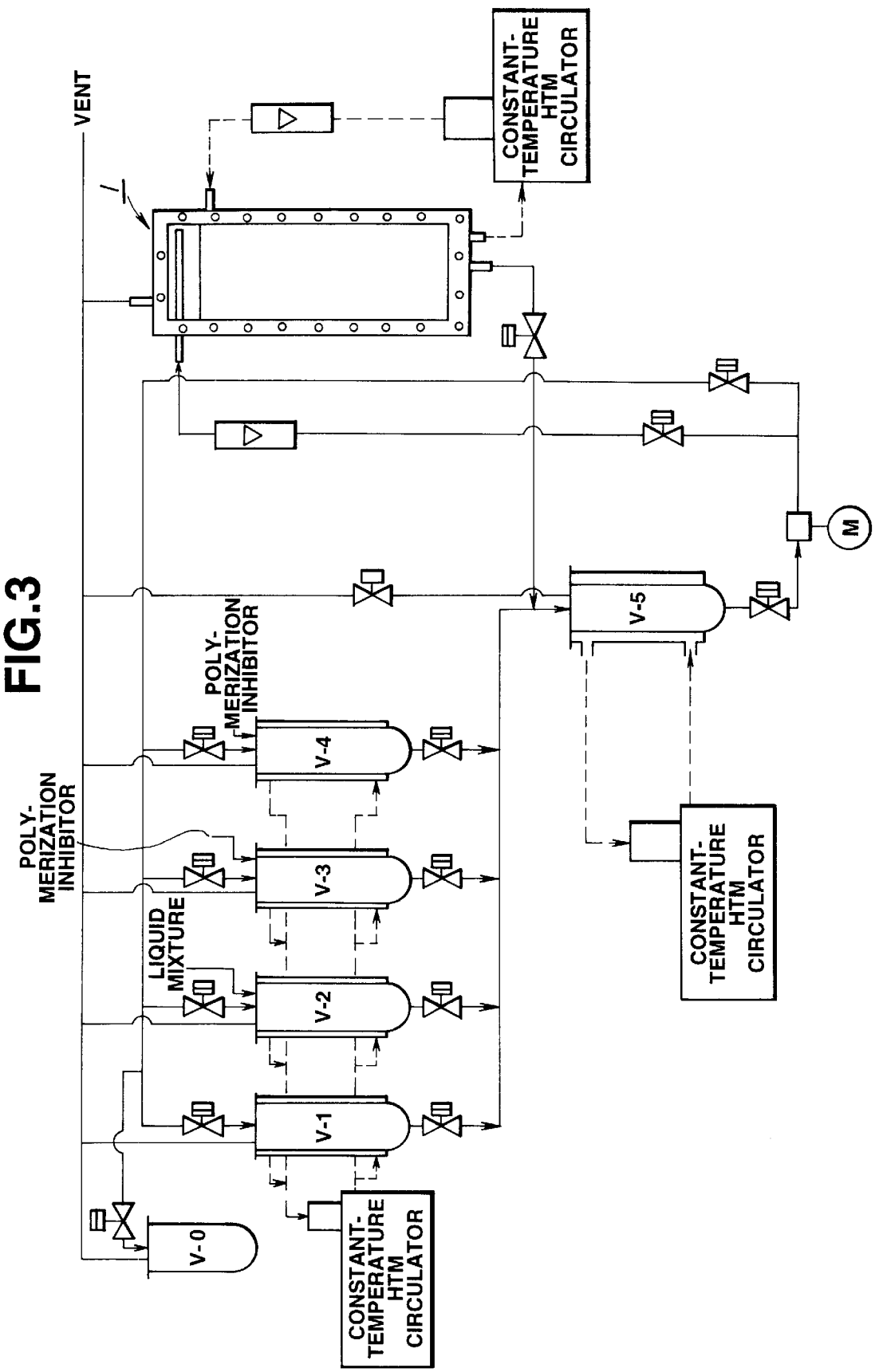
FIG. 3 is a diagram showing a crystallization system for carrying out a crystallization method according to the second preferred embodiment of the present invention.

FIG. 3 shows a multi-stage crystallization system incorporating the foregoing crystallizer 1 for performing the three-stage crystallization process. In the figure, symbols V-1 to V-4 denote first to fourth storage tanks, respectively. The fourth storage tank is a product storage tank for temporarily storing product acrylic acid. Symbol V-5 denotes a circulation tank whose liquid is circulated into the crystallizer 1. Symbol V-0 denotes a mother liquor storage tank where the mother liquor obtained through the crystallization using the liquid mixture with the lowest purity, that is, the liquid mixture in the first storage tank V-1, is temporarily stored as a waste liquid.

In this multi-stage crystallization system, acrylic acid containing impurities, such as acetic acid or propionic acid, and a polymerization inhibitor is first supplied into the second storage tank V-2 from outside of the system. The liquid mixture in the second storage tank V-2 is sent to the circulation tank V-5 and then circulated to the crystallizer 1 where the crystals of acrylic acid are formed. The mother liquor obtained through this process is sent to the first storage tank V-1 from the circulation tank V-5. Subsequently, the crystals are partially melted, or sweated and the sweated liquid is sent to the second storage tank V-2 from the circulation tank V-5.

Thereafter, the liquid in the third storage tank V-3 is sent to the circulation tank V-5 and then heated to the temperature higher than the freezing point of the crystals. The heated liquid is circulated into the crystallizer 1 to melt the crystals. The liquid in the third storage tank V-3 is the purified melt obtained by purifying the liquid mixture in the second storage tank V-2 through a process prior to the current crystallization process. A polymerization inhibitor feed pipe is provided at the third storage tank V-3 so that the purified melt in the third storage tank V-3 is mixed with the polymerization inhibitor in advance. Accordingly, melting of the crystals is performed in the presence of the polymerization inhibitor so that the melt of the crystals also contains the polymerization inhibitor. The melt thus obtained (that is, the mixture of the melted current crystals and the melt sent from the third storage tank V-3) is sent to the third storage tank V-3 from the circulation tank V-5. FIG. 4 is an explanatory diagram showing transfer flows of the liquids in the foregoing crystallization process.

Subsequently, crystallization is applied to the melt in the third storage tank V-3. This crystallization process is the same as the crystallization process for the liquid mixture in the second storage tank V-2 except that the storage tanks to which the obtained mother liquor, sweated liquid and purified melt are sent back are shifted by one stage. Specifically, the melt in the third storage tank V-3 is sent to the circulation tank V-5 and then to the crystallizer 1 where the crystallization is performed. Then, the mother liquor is sent to the second storage tank V-2 and the sweated liquid is sent to the third storage tank V-3. Further, the melt in the fourth storage tank V-4 is heated and circulated into the crystallizer 1 for melting the crystals, and the melted crystals along with the melt used to accelerate melting is recovered into the fourth storage tank V-4.

As appreciated, the melt in the fourth storage tank V-4 used to melt the crystals is obtained by purifying the melt in the third storage tank V-3 in a process prior to the current crystallization process. A polymerization inhibitor feed pipe is also provided at the fourth storage tank V-4 so that the melt in the fourth storage tank V-4 is mixed with the polymerization inhibitor in advance. Thus, melting of the crystals is performed in the presence of the polymerization inhibitor so that the melt from the current crystals also contains the polymerization inhibitor. The melt thus obtained is a product acrylic acid and sent to a large product storage tank (not shown) located outside the crystallization system. FIG. 5 is an explanatory diagram showing transfer of the liquids in the foregoing crystallization process.

Subsequent to the crystallization of the melt in the third storage tank V-3, crystallization is applied to the liquid mixture in the first storage tank V-1 (that is, the mother liquor obtained by the crystallization of the melt in the second storage tank V-2). This crystallization process is the same as the foregoing crystallization process, and the obtained mother liquor is sent to the mother liquor storage tank V-0 outside the crystallization system while the sweated liquid is sent to the first storage tank V-1. In the process of melting the crystals, the liquid mixture in the second storage tank V-2 is heated to melt the crystals, and the obtained melt is stored in the second storage tank V-2.

Subsequent to the crystallization of the liquid mixture in the first storage tank V-1, the crystallization of the liquid mixture in the second storage tank V-2 is performed so that one cycle of the crystallization process is completed. Specifically, in this preferred embodiment, during one cycle in the stationary operation of the system, the liquid mixture is first supplied into the second storage tank V-2 from outside of the system, the crystallization is applied to the liquid mixture in the second storage tank V-2 and then the crystallization is applied to the liquids in the third storage tank V-3, the first storage tank V-1 and the second storage tank V-2 successively. After such one cycle of the crystallization, the next cycle of crystallization is performed.

The crystallization is performed twice for the liquid in the second storage tank V-2 because the liquid mixture is supplied to the second storage tank V-2 from the outside of the system. Accordingly, one cycle process is composed of the three-stage crystallization including the second stage crystallization→the third stage crystallization→the first stage crystallization→the second stage crystallization.

Now, the third preferred embodiment of the present invention will be described hereinbelow with reference to FIG. 6.

FIG. 6 shows a multi-stage crystallization system incorporating the foregoing crystallizer 1 for performing the five-stage crystallization process. In the figure, symbol V-0' denotes a storage tank for temporary storage of the final mother liquor, symbols V-1' to V-5' denote storage tanks for intermediate liquid mixtures of the first to fifth stage crystallization, respectively. Symbol V-6' denotes a storage tank for temporary storage of a product and symbol V-7' denotes a circulation tank. The acrylic acid liquid mixture is supplied to the storage tank V-4'. In order to substantially equalize the amounts of the liquid mixtures, the amounts of the sweated liquids and the amounts of the crystals through the respective stages as in the threestage crystallization, the crystallization is performed in the order of 2→3→4→5→3→4→5→4→2→3→4→5→3→4→5→4→1→, wherein symbols V-n are simplified as n.

It is to be appreciated that the storage tank to which the liquid mixture is supplied from outside of the system is determined based on target purity and recovery of a product. Accordingly, it may be the first storage tank V-1 or the third storage tank V-3 in case of the three-stage crystallization, while it may be other than the fourth storage tank V-4 in case of the five-stage crystallization. Further, the number of the crystallization stages may be set equal to or more than six.

In the multi-stage crystallization where the liquid mixture containing the polymerization inhibitor is supplied to the storage tank other than that of the final stage, since the polymerization inhibitor is fed to the liquid mixture to be purified in the final stage, that is, the liquid mixture in the third storage tank V-3 in case of the three-stage crystallization or the liquid mixture in the fifth storage tank in case of the five-stage crystallization, it is not necessary to feed the polymerization inhibitor from the outside. For example, in case of the five-stage crystallization, if the polymerization inhibitor is put into the fifth-stage storage tank, the polymerization inhibitor is necessarily contained also in the fourth-stage storage tank since the mother liquor through the fifth-stage crystallization is sent to the fourth-stage storage tank, and similarly, the polymerization inhibitor is contained in the third-stage, second-stage and first-stage storage tanks. Further, in the crystallization of the lower stages, where the purity is lower than in the final stage, the melt of the higher stage is used in the process of melting the crystals so that the melt of the crystals contains the polymerization inhibitor even if the polymerization inhibitor is not substantially contained in the crystals.

In the crystallization at the final stage, melting of the crystals is performed using product acrylic acid. Since product acrylic acid is mixed with the polymerization inhibitor (the polymerization inhibitor is fed to the fourth storage tank V-4 in case of the three-stage crystallization and to the sixth storage tank V-6 in case of the five-stage crystallization), the melt necessarily contains the polymerization inhibitor.

On the other hand, in case of feeding the liquid mixture containing the polymerization inhibitor to the final-stage storage tank, if the polymerization inhibitor is fed only to the product storage tank (the fourth storage tank V-4 in case of the three-stage crystallization and the sixth storage tank V-6' in case of the five-stage crystallization), the polymerization inhibitor is contained in the storage tank of each stage.

As appreciated from the foregoing descriptions, by adding the polymerization inhibitor into the liquid mixture for the final stage crystallization and the product acrylic acid, polymerization of acrylic acid never occurs upon melting of the crystals, upon transferring the purified melt or while storing the purified melt. Thus, for example, even if a failure occurs in controlling the heating temperature of the melt, an accident such as explosion due to vigorous polymerization can be prevented. Further, supplying the polymerization inhibitor into the storage tank of each crystallization stage is not necessary. Thus, the plant and operations can be simplified, the crystallization time can be shortened and the supply amount of the polymerization inhibitor can be reduced.

On the other hand, if the polymerization inhibitor is simply fed per each crystallization stage, the process becomes complicated and the supply amount of the polymerization inhibitor is increased so that a large quantity of the polymerization inhibitor is contained in the mother liquor drained off from the lowest stage to outside of the system. Further, since the concentration of the polymerization inhibitor contained in the liquid mixture at the lower stage is increased, the freezing point decreases largely so that it becomes necessary to reduce the crystallization temperature or prolong the crystallization time.

A variety of compounds, for example, phenols, such as hydroquinone, p-methoxyphenol, cresol, phenol and t-butyl catechol, amines, such as diphenylamine, phenothiazine and methylene blue, copper compounds, manganate compounds may be used as polymerization inhibitor. Further, it is preferable to use those polymerization inhibitors under the atmosphere of a gas containing molecular oxygen.

For feeding the polymerization inhibitor to the product storage tank and the final-stage storage tank, a mixing tank for preparing inhibitor solution may be provided. Specifically, the final product (high-purity acrylic acid) is partly taken out and the polymerization inhibitor (solid) is dissolved thereinto so as to prepare a high-concentration inhibitor solution in the mixing tank. This high-concentration solution is transferred by a metering pump. The polymerization inhibitor is supplied to the final-stage storage tank after the melt is circulated to melt the crystals and the recovered liquid by melting the crystals is sent to the final-stage storage tank from the circulation tank. This avoids lowering of the concentration of the polymerization inhibitor due to addition of the melted crystals.

Since the product may be stored for a long time, the concentration of the polymerization inhibitor for the product is preferably higher than 20 ppm by weight, and more preferably higher than 50 ppm by weight. On the other hand, since the liquid in the intermediate storage tank is held for a relatively short time, it is sufficient that the concentration of the polymerization inhibitor is higher than 10 ppm by weight upon melting of the crystals. The polymerization inhibitor concentration is controlled by on-line monitoring of the concentrations of the polymerization inhibitor in the product storage tank and the final-stage storage tank (V-6 and V-5 in case of the five-stage crystallization) or by periodically sampling the liquids and measuring the concentrations of the polymerization inhibitor, and then by adjusting the supply amount of the high-concentration polymerization inhibitor solution from the foregoing mixing tank. However, in actual industrial operations, the amount of the feed liquid mixture, the product yield, the final mother liquor and the material balance of the feed liquid mixture, the mother liquor, the sweated liquid, the crystals in each stage are precisely calculated and controlled so that the supply amount of the polymerization inhibitor can be set in advance to satisfy the foregoing concentrations.

EXAMPLES

The results of some experiments will be described hereinbelow.

Example 1

The crystallization system shown in FIG. 3 was used, and the three-stage crystallization was performed using acrylic acid containing impurities as a feed liquid mixture. As the crystallizer, the vertical plate type crystallizer as shown in FIG. 1 was used. Size of the crystallizer plate was 200 mm in width and 600 mm in height. In front of the crystallizer, a transparent poly (vinyl chloride) plate was placed for visual observations. A 30% by weight ethanol aqueous solution was used as a heat transfer medium. In the first to third storage tanks V-1 to V-3, the liquids obtained through crystallization, sweating process and melting process performed in advance were stored. 4-methoxyphenol (methylhydroquinone) was added as a polymerization inhibitor to acrylic acid stored in the storage tank V-3 so as to be 100 ppm by weight. Further, the same polymerization inhibitor was added to feed acrylic acid and product acrylic acid in the tank V-4 so as to be 100 ppm by weight.

Feed acrylic acid containing the impurities was supplied to the second storage tank V-2. In the second-stage crystallization, 766 g of the mother liquor from the third-stage crystallization, 754 g of the melt from the first-stage crystallization, 168 g of the sweated liquid from the second-stage crystallization and 1,520 g of feed acrylic acid were mixed to produce 3,208 g of the liquid mixture. The liquid mixture was divided into two halves to be crystallized twice. Through one operation of the second-stage crystallization, 1,604 g of the liquid mixture was used, and 763 g of the mother liquor, 84 g of the sweated liquid and 757 g of the melt were obtained. Upon melting the crystals, 200 g of the liquid in the third storage tank V-3 was supplied to the circulation tank V-5 and then circulated to the crystallizer 1 to melt all the crystals. As a result, through two operations in the second-stage crystallization, 1,526 g of the mother liquor was obtained and was sent to the first storage tank V-1, 168 g of the sweated liquid was obtained and was sent to the second storage tank V-2, and 1,514 g of the melt was obtained and was sent to the third storage tank V-3.

In the third-stage crystallization, 1,514 g of the melt from the second-stage crystallization and 84 g of the sweated liquid from the third-stage crystallization were mixed to produce 1,598 g of the liquid mixture, and 760 g of the mother liquor, 84 g of the sweated liquid and 754 g of the melt were obtained. The mother liquor was sent to the second storage tank V-2, the sweated liquid was sent to the third storage tank V-3 and the melt was sent to the product temporary storage tank V-4. Similar to the second-stage crystallization, the liquid in the storage tank V-4 was circulated to melt the crystals.

Similarly, in the first-stage crystallization, 1,526 g of the mother liquor from the second-stage crystallization and 84 g of the sweated liquid were mixed to produce 1,610 g of the liquid mixture, and 766 g of the mother liquor, 84 g of the sweated liquid and 760 g of the melt were obtained. Melting of the crystals was performed while circulating the liquid in the second storage tank V-2. The mother liquor was sent to the final mother liquor temporary storage tank V-0, the sweated liquid was sent to the first-stage tank V-1 and the melt was sent to the second storage tank V-2. In this manner, one crystallization cycle was completed by performing the first-stage crystallization once, the second-stage crystallization twice and the third-stage crystallization once, and 754 g of the product and 766 g of the final mother liquor were obtained from 1,520 g of the feed liquid mixture. Through the whole-stage crystallization, the temperatures of the heat transfer medium were controlled to be 2° C., 15° C. and 25° C. during the crystallization, the sweating and the melting steps, respectively. The foregoing operations were continued for 5 days and no polymerization occurred.

Comparative Example 1

The experiment was conducted in the same manner as in Example 1 except that the polymerization inhibitor was not fed to the storage tank V-3. Acrylic acid in the storage tanks V-2 and V-3 polymerized vigorously. According to analysis before polymerization, the concentration of the polymerization inhibitor in the tank V-2 was 5 ppm, while that in the tank V-3 was 1 ppm. On the other hand, in Example 1, the concentration of the polymerization inhibitor in the tank V-2 was 80 ppm, while that in the tank V-3 was 30 ppm immediately after melting the crystals.

Example 2

Glass double tubes with 40 mm inner diameter for an inner tube, 70 mm outer diameter for an outer tube, a length of 800 mm were used as a crystallizer. The crystallization was performed by supplying acrylic acid onto an inner surface of the inner tube as a film and by supplying the cooling medium between the inner and outer tubes. 900 g of feed acrylic acid was used as the feed mixture. 600 g of crystals was obtained and the mother liquor was drained off. Then, 200 g of purified acrylic acid containing 200 ppm of 4-methoxyphenol as a polymerization inhibitor was supplied to the circulation tank, and the crystals were melted while circulating it onto the crystals.

Subsequently, 800 g of the obtained melt was used as the feed liquid mixture, and 600 g of the crystals was obtained. 200 g of purified acrylic acid containing 200 ppm of the polymerization inhibitor was supplied to the circulation tank. Melting of the crystals was performed while circulating it onto the crystals. The obtained melt could be preserved for a long term at 15° C.

Comparative Example 2

Using the same crystallizer as in Example 2,800 g of the crystals was separated from 1,000 g of feed acrylic acid. Then, the crystals were melted by raising a temperature of the heat transfer medium to 25° C. without circulating the melt. Further, using this melt of the crystals as the feed liquid mixture, 600 g of the crystals was separated and then melted in the same manner. While preserving this melt, very vigorous polymerization occurred. According to analysis prior to polymerization, a polymerization inhibitor concentration in the melt was 6 ppm.

Example 3

Using the crystallization system shown in FIG. 6, the five-stage crystallization was performed. Feed acrylic acid was supplied to the tank V-4'.

In order to substantially equalize the amounts of the liquid mixtures, the sweated liquids and the crystals through the respective stages as in Example 1, it was found preferable to perform the crystallization in the order of 2→3→4→5→3→4→5→4→2→3→4→5→3→4→5→4→1→.

In this example, the polymerization inhibitor (4-methoxyphenol) was added, in advance, to the acrylic acid in the tank V-4' and the product acrylic acid in the tank V-6' so as to be 100 ppm, respectively. In addition, the polymerization inhibitor was added to the tank V-5' so as to be 100 ppm, while no polymerization inhibitor was added to the tanks V-0' to V-3'. In this condition, the foregoing 17 stage process was repeated five times. No polymerization occurred, and all the operations of each stage were successfully performed.

As appreciated from the foregoing description, the crystallizer is not limited to the plate type crystallizer and, for example, the tube type crystallizer as used in Example 2 may also be used as a crystallizer. And other types of crystallizers may also be used. As a feed liquid mixture, not only acrylic acid, but also other polymerizable compounds such as methacrylic acid may also be used.

While the present invention has been described in terms of the preferred embodiments, the invention is not to be limited thereto, but can be embodied in various ways without departing from the principle of the invention as defined in the appended claims.

What is claimed is:

1. A crystallization method, wherein, after cooling a liquid mixture containing a crystallizable component, forming crystals of said component and separating said crystals, the separated crystals are melted and recovered as a melt to purify said component, the method comprising the steps of:

adding a polymerization inhibitor to a purified melt whose purity is substantially equal to that of said separated crystals;

heating said purified melt to a temperature higher than a freezing point of said crystals;

sending said heated melt to said crystals so as to melt said crystals; and recovering the melted crystals along with said purified melt containing said polymerization inhibitor.

2. The crystallization method according to claim 1, wherein said polymerization inhibitor is added to said purified melt so that a concentration of the polymerization inhibitor in a sum of the melted crystals and the purified melt becomes higher than 10 ppm by weight.

3. A crystallization method comprising:

a crystallization step of cooling a liquid mixture containing a crystallizable component, forming crystals of said component and separating said crystals; and a melting step of the separated crystals and recovering a melt of said crystals;

said crystallization and melting steps performed in a multi-stage manner to achieve multi-stage crystallization so as to gradually increase purity of said crystallizable component, wherein, in said crystallization step at a final purification stage of said multi-stage crystallization, a liquid mixture containing a polymerization inhibitor is used, and wherein, in said melting step at the final purification stage of said multi-stage crystallization, a polymerization inhibitor is added to a purified melt obtained in advance through said melting step at the final purification stage, and the purified melt is heated and sent onto the separated crystals so as to melt all the separated crystals, and the melted crystals are recovered along with the purified melt containing the polymerization inhibitor.

4. The crystallization method according to claim 3, wherein said polymerization inhibitor is added to said purified melt so that a concentration of the polymerization inhibitor in a sum of the melted crystals and the purified melt becomes higher than 10 ppm by weight.

5. A crystallization method performing multi (N−1) stage crystallization (N being an integer), using a crystallization system having a crystallizer equipped with first to Nth (3≦N) liquid storage tanks, which contain intermediate liquids gradually purified by multi-stage crystallization, comprising the steps of:

(a) supplying a crystallizable liquid mixture to the Kth (K<N; K is a given integer) liquid storage tank (K being an integer less than N) from outside the crystallization system;

(b) carrying out crystallization using a liquid mixture in the Kth liquid storage tank as a crystallization feed liquid so as to send a residual liquid to the (K−1)th liquid storage tank after completion of said crystallization;

(c) heating a liquid mixture in the (K+1)th liquid storage tank and then circulating the heated liquid onto the crystal to melt the crystal;

(d) storing a mixture of the crystal melt of step (c) and heated circulating liquid in the (K+1)th liquid storage tank;

(e) performing the (N−1)-stage crystallization to achieve said process steps using the liquid mixtures in the first to (N−1)th liquid storage tanks as crystallization feed liquids where the Nth liquid storage tank is used to store a final product;

the improvement characterized by:

supplying a polymerization inhibitor only to the (N−1)th and Nth liquid storage tanks when K≦(N−2), where the Kth tank is the liquid storage tank to which the crystallizable liquid mixture is supplied from outside the crystallization system, while supplying the polymerization inhibitor only to the Nth liquid storage tank when K=(N−1).

6. The crystallization method according to claim 1, wherein, after the crystals of the liquid mixture in the Kth storage tank are separated, partial melting of the crystals is performed before melting all the separated crystals, and wherein the melt of the crystals obtained by said partial melting is stored in the Kth storage tank.

* * * * *